United States Patent

Aigner et al.

Patent Number: 5,292,942
Date of Patent: Mar. 8, 1994

[54] PROCESS FOR THE PREPARATION OF AQUEOUS BETAINE SOLUTIONS

[75] Inventors: Rudolf Aigner, Burgkirchen; Guillermo Maier, Haiming; Rainer Müller, Burghausen; Hubert Seitz, Burgkirchen, all of Fed. Rep. of Germany

[73] Assignee: Hoechst Aktiengesellschaft, Frankfurt, Fed. Rep. of Germany

[21] Appl. No.: 42,115

[22] Filed: Apr. 2, 1993

[30] Foreign Application Priority Data

Apr. 3, 1992 [DE] Fed. Rep. of Germany ....... 4211190

[51] Int. Cl.$^5$ .......................................... C07C 229/00
[52] U.S. Cl. ...................... 562/575; 554/52; 562/561; 562/564; 562/567
[58] Field of Search ............... 562/575, 561, 564, 567; 554/52

[56] References Cited

U.S. PATENT DOCUMENTS

| | | | |
|---|---|---|---|
| 2,082,275 | 6/1937 | Daimler | 562/575 |
| 2,129,264 | 9/1938 | Downing | 562/575 |
| 2,564,507 | 8/1951 | Schaeffer | 562/575 |
| 2,800,502 | 7/1957 | Vassel | 562/575 |
| 3,480,665 | 11/1969 | Nagy | 562/575 |
| 3,555,079 | 1/1971 | Marumo | 562/575 |
| 3,649,677 | 3/1972 | Morris | 562/575 |
| 3,819,539 | 6/1974 | Bloch et al. | |
| 3,954,845 | 5/1976 | Martinsson | 562/575 |
| 4,497,825 | 2/1985 | Bade | |
| 4,832,871 | 5/1989 | Bade | 562/575 |
| 5,075,498 | 12/1991 | Perine | 562/575 |

FOREIGN PATENT DOCUMENTS 464657 4/1937 United Kingdom.
1185111 3/1972 United Kingdom.

OTHER PUBLICATIONS

Derwent Abstract No. 90-038321/06/, corresponding to EP-A-0353580 (Jul. 24, 1989).

Primary Examiner—Michael L. Shippen
Attorney, Agent, or Firm—Connolly & Hutz

[57] ABSTRACT

A process is described for the preparation of aqueous solutions of betaines of the formula $$R^1-\underset{\underset{R^3}{|}}{\overset{\overset{R^2}{|}}{N^+}}-(CH_2)_y-COO^-$$

in which: $R^1$ is an alkyl radical having 6 to 22 carbon atoms or is a radical of the formula $R'CONH(CH_2)_z-$, in which $R'$ has the meaning of $R^1$ and z is 2, 3 or 4, $R^2$ is an alkyl radical having 1 to 4 carbon atoms or is a radical of the formula $-(CH_2)_m-OH$, in which m is 1, 2 or 3, $R^3$ is an alkyl radical having 1 to 4 carbon atoms or is a radical of said formula $-(CH_2)_m-OH$ and y is 1, 2 or 3. The aqueous betaine solutions are prepared by quaternization of the corresponding tertiary amines with an ω-halocarboxylic acid and with an alkali metal hydroxide in the aqueous phase. The quaternization is carried out continuously in two or three stirred tanks arranged in a cascade, defined process characteristics being maintained in each tank. Using the novel process, aqueous betaine solutions are obtained in high yield and purity in a simple manner.

13 Claims, No Drawings

PROCESS FOR THE PREPARATION OF AQUEOUS BETAINE SOLUTIONS

DESCRIPTION

The invention relates to a process for the preparation of aqueous solutions of betaines of the formula 1

$$R^1-\overset{\overset{R^2}{|}}{\underset{\underset{R^3}{|}}{N^+}}-(CH_2)_y-COO^- \quad (1)$$

in which: $R^1$ is an alkyl radical having 6 to 22 carbon atoms, preferably 8 to 18 carbon atoms, or is a radical of the formula $R'CONH(CH_2)_z-$, in which $R'$ has the meaning of $R^1$ and z is 2, 3 or 4, $R^2$ is an alkyl radical having 1 to 4 carbon atoms or is a radical of the formula $-(CH_2)_m-OH$, in which m is 1, 2 or 3, $R^3$ is an alkyl radical having 1 to 4 carbon atoms or is a radical of said formula $-(CH_2)_m-OH$ and y is 1, 2 or 3,
by reaction of a tertiary amine of the formula 2

$$R^1-NR^2R^3 \quad (2)$$

in which $R^1$, $R^2$ and $R^3$ have the meanings given above, with an ω-halocarboxylic acid of the formula 3

$$X-(CH_2)_y-COOH \quad (3)$$

in which X is a halogen, preferably Cl, and y has the abovementioned meaning,
and with alkali metal hydroxide in the aqueous phase.

The preparation of aqueous solutions of betaines by reaction (quaternization) of tertiary amines with an ω-halocarboxylic acid and alkali metal hydroxide in the aqueous phase has already been known for a long time, for example from the two U.S. Pat. Nos. 3,819,539 and 4,497,825.

It is based on the following overall reaction equation (the reaction components are dimethyllaurylamine, monochloroacetic acid and sodium hydroxide):

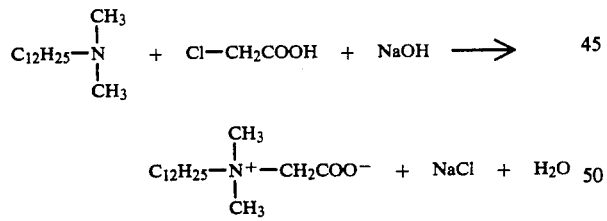

The resulting aqueous solutions essentially comprise the desired betaine, the alkali metal halogen salt formed and the water used and the water formed and generally have an active compound content of 20 to 70% by weight, preferably 25 to 60% by weight. These aqueous betaine solutions already represent valuable products as such, in particular for the personal hygiene sector. Betaines have namely not only good cleansing properties, but also good skin tolerance. However, the skin tolerance is only obtained if the betaine solution contains only very little starting amine, since negative skin effects seem to start particularly from this.

In the preparation of the aqueous betaine solutions in question, the principle concern is therefore to achieve as high as possible a conversion of the tertiary amine used with a simultaneously high yield of betaine. The resulting aqueous betaine solution should contain less than 2 mol-%, preferably less than 1 mol-%, of (unreacted) tertiary amine, based on tertiary amine used (starting amine). It has already been frequently attempted to achieve this aim by special measures, for example by maintaining a defined pH during the quaternization, by bringing together the reaction components tertiary amine, halocarboxylic acid and alkali metal hydroxide in a highly defined sequence by, for example, introducing the tertiary amine and the halocarboxylic acid and slowly adding the alkali metal hydroxide or by introducing the halocarboxylic acid and the alkali metal hydroxide and adding the tertiary amine, in addition by the use of special solvents and/or by maintaining a relatively low temperature during the reaction. Using the known processes, therefore, the desired aim of bringing the amine contamination of the resulting aqueous betaine solutions to the stated mol-% values is achieved, if at all, only by means of more or less laborious measures. In addition, these processes can only be carried out discontinuously.

The object of the invention is accordingly to provide a process for the preparation of the aqueous betaine solutions mentioned in the introduction which supplies the betaines in high yield and high purity, that is aqueous betaine solutions having less than 2 mol-% of starting amine, preferably less than 1 mol-%, based on tertiary amine used. The novel process, in addition, is to be able to be carried out continuously in a simple manner.

The process according to the invention comprises carrying out the reaction continuously in two- or three stirred tanks arranged in a cascade and proceeding in such a way that a) the first stirred tank is supplied simultaneously and continuously with the tertiary amine and the ω-halocarboxylic acid in an amount of 1 to 1.3 mol per mole of tertiary amine, preferably 1 to 1.15 mol per mole of tertiary amine, the alkali metal hydroxide in an amount of only 0.80 to 0.98 mol per mole of ω-halocarboxylic acid, preferably 0.85 to 0.95 mol per mole of ω-halocarboxylic acid, and the water in an amount such that the betaine content of the finished aqueous betaine solution is 20 to 50% by weight, preferably 25 to 40% by weight, and in this tank at a temperature of 60° to 100° C., preferably 70° to 95° C., a residence time is maintained such that the product leaving this tank and entering the second stirred tank still contains 2 to 15 mol-% of tertiary amine, preferably 3 to 10 mol-% of tertiary amine, based on tertiary amine used, and b) the second stirred tank is continuously supplied with a further amount of alkali metal hydroxide which is in the range from the residue of the stoichiometric amount of alkali metal hydroxide remaining from the first tank to an excess of 5 mol-% (based on ω-halocarboxylic acid used), preferably 3 mol-%, and in this tank at a temperature of 60° to 100° C., preferably 70° to 95° C., a residence time is maintained such that the aqueous betaine solution leaving the tank contains less than 2 mol-% of tertiary amine, preferably less than 1 mol-% of tertiary amine, based on tertiary amine used, where, when three stirred tanks are used, the third is used for a following reaction at a temperature of 70° to 100° C., preferably 80° to 100° C., in order to obtain an aqueous betaine solution which, in comparison with the betaine solution from the second stirred tank, has a still lower content of tertiary starting amine.

The process according to the invention is therefore carried out continuously in two or three stirred tanks arranged one after the other, the desired (finished) aqueous betaine solution being withdrawn from the second tank or from the third tank. In the first stirred tank, the alkali metal hydroxide is not added in the stoichiometrically required amount—based on ω-halocarboxylic of 80 to 98 mol-%, preferably 85 to 95 mol-%. In addition, in the first stirred tank the reaction proceeds up to a defined degree of conversion. The aqueous reaction mixture flowing from this tank is still to contain 2 to 15 mol-% of the tertiary amine used, preferably 3 to 10 mol-%. In the first tank, therefore, the reaction is carried out using a deficit of alkali metal hydroxide and the reaction is performed up to the stated amine content. In the second stirred tank, further alkali metal hydroxide is added to the reaction mixture, that is the amount of alkali metal hydroxide remaining relative to the stoichiometric amount in the first stirred tank and, if required, alkali metal hydroxide exceeding this up to a stoichiometric excess—based on ω-halocarboxylic acid used—of 5 mol-%, preferably 3 mol-%. The alkali metal hydroxide continuously supplied to the second reaction tank therefore includes the remainder of the stoichiometric amount mentioned and the excess mentioned. If an aqueous betaine solution is desired in the second stirred tank having a very low content of starting amine, not only the remainder of the stoichiometric amount of alkali metal hydroxide will be added in the second stirred tank but also the excess amount mentioned; as a result, a very high conversion of the tertiary amine used is achieved even with two stirred tanks. A third stirred tank will be used if it is desired to prepare a particularly pure betaine solution. The aqueous betaine solution entering the third tank will then be further reacted at the stated-temperature, that is 70° to 100° C., preferably 80° to 100° C., until the desired low amine value is reached. To achieve these particularly low amine values, it can be advantageous to add further alkali metal hydroxide continuously in the third stirred tank also. The addition of alkali metal hydroxide in the third stirred tank is preferably carried out when only the remaining stoichiometric amount of alkali metal hydroxide has been added in the second stirred tank. In such a case, the excess of alkali metal hydroxide mentioned of up to 5 mol-%, preferably of up to 3 mol-%, based on monohalocarboxylic acid used, will therefore be added to the third stirred tank.

As a result of the temperatures to be maintained, the reaction proceeds at atmospheric pressure or a slight superatmospheric pressure. The mean total residence time is about 10 to 25 hours. A special work-up of the aqueous betaine solution withdrawn from the second or third stirred tank is not required, since—as mentioned in the introduction—these solutions are used as such. Their pH is generally adjusted to 7 to 8, for example by addition of hydrochloric acid.

The tertiary starting amines correspond to the formula 2 given in the introduction. The long alkyl radical $R^1$ can also contain double bonds, preferably 1 to 3. Preferred starting amines are those of the formula 2, when $R^1$ is an alkyl radical having 8 to 18 carbon atoms or is a radical of the formula $R'CONH(CH_2)_z-$, in which $R'$ has the meaning mentioned of $R^1$ and z is 2, 3 or 4, and $R^2$ and $R^3$ are each methyl. Examples which may be mentioned are: dimethyloctylamine, dimethyllaurylamine, dimethylstearylamine, dimethyl coconut alkylamine, dimethyl tallow alkylamine and the like and lauroylaminopropyldimethylamine, stearoylaminopropyldimethylamine, coconut acylaminopropyldimethylamine and the like. The ω-halocarboxylic acid is preferably monochloroacetic acid. The alkali metal hydroxide is preferably sodium hydroxide or potassium hydroxide. The alkali metal hydroxide is preferably used in the form of an aqueous solution, that is in a 15 to 70% by weight aqueous solution, preferably in a 20 to 50% by weight solution. The total amount of water (solvent) is selected, as already described above, so that the concentration of active compound (betaine) in the finished aqueous betaine solution is about 20 to 50% by weight, preferably 25 to 40% by weight. The expression "aqueous" betaine solution also includes such solutions which, apart from. water, also contain other solvents, for example methanol, ethanol, propanol and/or isopropanol.

The process according to the invention has a series of advantages. It can be carried out continuously and gives, in comparison to discontinuous processes, a significantly higher space-time yield. In addition, it gives a virtually complete conversion of the tertiary amine used and simultaneously very pure aqueous betaine solutions. Aqueous betaine solutions can thus be obtained which contain less than 2 mol-% or less than 1 mol-% of tertiary amine, based on the molar amount used of tertiary amine, or even those betaine solutions which are virtually free from tertiary starting amine. The betaine solutions are also very pure with regard to halocarboxylic acid and salts thereof, for example monochloroacetate, and with regard to hydroxycarboxylic acids, for example glycolic acid. Using the process according to the invention, it is therefore possible to prepare the betaine in high yield and high purity in a simple manner.

The invention is now described in more detail with examples.

EXAMPLE 1

The reaction was carried out in two stirred tanks each of volume 8 m$^3$ arranged in a cascade. Each of the two tanks was furnished with an agitator, a thermometer and a cooling jacket (removal of the heat of reaction liberated using cooling water). The first stirred tank was continuously supplied per hour via four inlet ports with: 226 kg (1.0 kmol) of dimethylalkylamine (alkyl=approximately 70% $C_{12}$, 25% $C_{14}$ and 5% $C_{16}$), 118.1 kg (1.0 kmol) of 80% MCA (MCA=monochloroacetic acid) and 68 kg of 50% by weight aqueous sodium hydroxide solution, that is 0.85 kmol of NaOH per kmole of MCA, and additional water, that is 712 kg, so that a roughly 25% by weight solution of active compound (betaine) resulted. Since the stoichiometric amount of NaOH, based on MCA used, is 1.0 kmol, only 85 mol-% of the stoichiometrically required amount was added by the 0.85 kmol of NaOH per kmole of MCA to the first stirred tank, which corresponds to a stoichiometric alkali difference of 0.15 kmol or 15 mol-%. The remaining amount of alkali missing from the first stirred tank of 0.15 kmol (that is 12.0 kg of 50% by weight sodium hydroxide solution) was continuously supplied per hour to the second stirred tank. In the first stirred tank, a temperature of 95° C. was maintained and in the second tank a temperature of likewise 95° C. was maintained (both tanks were operated at atmospheric pressure). The mean residence time over both stirred tanks was 14 hours. The product (product mixture)

leaving the first tank had a free amine content of 9 mol-% and the product leaving the second tank had a content of 1.8 mol-%, based on the dimethylalkylamine used.

EXAMPLE 2

The reaction was carried out in the two stirred tanks cited in Example 1. The first stirred tank was continuously supplied per hour with: 220 kg (1.0 kmol) of dimethyllaurylamine (lauryl=>98% $C_{12}$), 129.9 kg (1.1 kmol) of 80% MCA and 79.2 kg of 50% by weight aqueous sodium hydroxide solution, that is 0.9 kmol of NaOH per kmole of MCA, and additional water, that is 425 kg, so that a roughly 35% by weight solution of betaine resulted. Since the stoichiometric amount of NaOH, based on MCA used, is 1.1 kmol, only 90 mol-% of the stoichiometrically required amount was added by the 0.9 kmol of NaOH per kmole of MCA to the first stirred tank, which corresponds to a stoichiometric alkali difference of 0.10 kmol or 10 mol-%. The remaining amount of alkali missing from the first stirred tank of 0.10 kmol (that is 8.8 kg of 50% by weight sodium hydroxide solution) was continuously supplied per hour to the second stirred tank. In the first stirred tank, a temperature of 70° C. was maintained and in the second tank a temperature of likewise 70° C. was maintained (both tanks were operated under atmospheric pressure). The mean residence time over both stirred tanks was 18 hours. The product leaving the first tank had a free amine content of 5 mol-% and the product leaving the second tank had a content of 0.9 mol-%, based on the dimethyllaurylamine used.

EXAMPLE 3

The reaction was carried out in the two stirred tanks cited in Example 1. The first stirred tank was continuously supplied per hour with: 226 kg (1.0 kmol) of dimethylalkylamine (alkyl=approximately 70% $C_{12}$, 25% $C_{14}$ and 5% $C_{16}$), 135.8 kg (1.15 kmol) of 80% MCA and 87.5 kg of 50% by weight aqueous sodium hydroxide solution, that is 0.95 kmol of NaOH per kmole of MCA, and additional water, that is 462 kg, so that a roughly 30% by weight solution of betaine resulted. Since the stoichiometric amount of NaOH, based on MCA used, is 1.15 kmol, only 95 mol-% of the stoichiometrically required amount was added by the 0.95 kmol of NaOH per kmole of MCA to the first stirred tank, which corresponds to a stoichiometric alkali difference of 0.05 kmol or 5 mol-%. The remaining amount of alkali missing from the first stirred tank of 0.05 kmol and additional 0.03 kmol of NaOH as excess (that is 7.4 kg of 50% by weight sodium hydroxide solution) was continuously supplied per hour to the second stirred tank. In the first stirred tank, a temperature of 95° C. was maintained and in the second tank a temperature of likewise 95° C. was maintained (both tanks were operated under atmospheric pressure). The mean residence time over both stirred tanks was 17 hours. The product leaving the first tank had a free amine content of 3 mol-% and the product leaving the second tank had a content of 0.5 mol-%, based on the dimethylalkylamine used.

EXAMPLE 4

The reaction was carried out in three stirred tanks each of volume 8 m³ arranged in a cascade. Each of the three tanks was furnished with an agitator, a thermometer and a cooling jacket. The first stirred tank was continuously supplied per hour via four inlet ports with: 226 kg (1.0 kmol) of dimethylalkylamine (alkyl=approximately 70% $C_{12}$, 25% $C_{14}$ and 5% $C_{16}$), 124.1 kg (1.05 kmol) of 80% MCA and 79.8 kg of 50% by weight aqueous sodium hydroxide solution, that is 0.95 kmol of NaOH per kmole of MCA, and additional water, that is 462 kg, so that a roughly 30% by weight solution of betaine resulted. Since the stoichiometric amount of NaOH, based on MCA used, is 1.05 kmol, only 95 mol-% of the stoichiometrically required amount was added by the 0.95 kmol of NaOH per kmole of MCA to the first stirred tank, which corresponds to a stoichiometric alkali difference of 0.05 kmol or 5 mol-%. The remaining amount of alkali missing from the first stirred tank of 0.05 kmol (that is 4.2 kg of 50% by weight sodium hydroxide solution) was continuously supplied per hour to the second stirred tank. The third stirred tank was additionally supplied with an excess of 0.03 kmol of alkali, based on MCA (that is 2.5 kg of 50% by weight sodium hydroxide solution/hour). In the first stirred tank, a temperature of 90° C. was maintained, in the second tank a temperature of 95° C. was maintained and in the third tank a temperature of 98° C. was maintained (all tanks were operated under atmospheric pressure). The mean residence time over all stirred tanks was 25 hours. The product leaving the first tank had a free amine content of 6 mol-%, the product leaving the second tank had a content of 0.6 mol-% and the product leaving the third tank had a free amine content of 0.2 mol-%, based on the dimethylalkylamine used.

EXAMPLE 5

The reaction was carried out in three stirred tanks cited in Example 4. The first stirred tank was continuously supplied per four via four inlet ports with: 317 kg (1.0 kmol) of N-coconut fatty acid amidopropyl-N-N-dimethylamine (amidamine), 129.9 kg (1.1 kmol) of 80% MCA and 83.6 kg of 50% by weight aqueous sodium hydroxide solution, that is 0.95 kmol of NaOH per kmole of MCA, and additional water, that is 745 kg, so that a roughly 30% by weight solution of betaine resulted. Since the stoichiometric amount of NaOH, based on MCA used, is 1.10 kmol, only 95 mol-% of the stoichiometrically required amount was added by the 0.95 kmol of NaOH per kmole of MCA to the first stirred tank, which corresponds to a stoichiometric alkali difference of 0.05 kmol or 5 mol-%. The remaining amount of alkali missing from the first stirred tank of 0.05 kmol (that is 4.4 kg of 50% by weight sodium hydroxide solution) was continuously supplied per hour to the second stirred tank. The third stirred tank was further supplied with an excess of 0.05 kmol of alkali, based on MCA (that is 4.4 kg of 50% by weight sodium hydroxide solution/ hour). In the first stirred tank, a temperature of 90° C. was maintained, in the second tank a temperature of 95° C. was maintained and in the third tank a temperature of 98° C. was maintained (all tanks were operated under atmospheric pressure). The mean residence time over all stirred tanks was 18 hours. The product leaving the first tank had a free amine content of 4 mol-%, the product leaving the second tank had a content of 0.4 mol-% and the product leaving the third tank had a free amine content of 0.2 mol-%, based on the amidamine used.

Examples 1 to 5 are summarized in the following table.

TABLE

| Example | Tertiary starting amine (kmol) | MCA (kmol) | NaOH based on MCA (kmol) | | | Residual amine, based on amine used (mol-%) | | | Temperature (°C.) | Residence time (hours) | Betaine content (% by weight) |
| --- | --- | --- | --- | --- | --- | --- | --- | --- | --- | --- | --- |
| | | | 1st ST | 2nd ST | 3rd ST | 1st ST | 2nd ST | 3rd ST | | | |
| 1 | 1 | 1 | 0.85 | 0.15 | — | 9 | 1.8 | — | 95/95 | 14 | 25 |
| 2 | 1 | 1.10 | 0.90 | 0.10 | — | 5 | 0.9 | — | 70/70 | 18 | 35 |
| 3 | 1 | 1.15 | 0.95 | 0.08 | — | 3 | 0.5 | — | 95/95 | 17 | 30 |
| 4 | 1 | 1.05 | 0.95 | 0.05 | 0.03 | 6 | 0.6 | 0.2 | 90/95/98 | 25 | 30 |
| 5 | 1 | 1.10 | 0.95 | 0.05 | 0.05 | 4 | 0.4 | 0.2 | 90/95/98 | 18 | 30 |

MCA = Monochloroacetic acid
ST = Stirred tank

We claim:

1. A process for the preparation of aqueous solutions of betaines of the formula 1

$$R^1\text{---}\underset{\underset{R^3}{|}}{\overset{\overset{R^2}{|}}{N^+}}\text{---}(CH_2)_y\text{---}COO^- \quad (1)$$

in which: $R^1$ is an alkyl radical having 6 to 22 carbon atoms or is a radical of the formula $R'CONH(CH_2)_z\text{---}$, in which $R'$ has the meaning of $R^1$ and z is 2, 3 or 4, $R^2$ is an alkyl radical having 1 to 4 carbon atoms or is a radical of the formula $\text{---}(CH_2)_m\text{---}OH$, in which m is 1, 2 or 3, $R^3$ is an alkyl radical having 1 to 4 carbon atoms or is a radical of said formula $\text{---}(CH_2)_m\text{---}OH$ and y is 1, 2 or 3,
by reaction of a tertiary amine of the formula 2

$$R^1\text{---}NR^2R^3 \quad (2)$$

in which $R^1$, $R^2$ and $R^3$ have the meanings given above, with an ω-halocarboxylic acid of the formula 3

$$X\text{---}(CH_2)_y\text{---}COOH \quad (3)$$

in which X is a halogen and y has the above-mentioned meaning,
and with alkali metal hydroxide in the aqueous phase, which comprises carrying out the reaction continuously in two or three stirred tanks arranged in a cascade and proceeding in such a way that a) the first stirred tank is supplied simultaneously and continuously with the tertiary amine and the ω-halocarboxylic acid in an amount of 1 to 1.3 mol per mole of tertiary amine, the alkali metal hydroxide in an amount of only 0.80 to 0.98 mol per mole of ω-halocarboxylic acid and the water in an amount such that the betaine content of the finished aqueous betaine solution is 20 to 50% by weight, and in this tank at a temperature of 60 to 100° C. a residence time is maintained such that the product leaving this tank and entering the second stirred tank still contains 2 to 15 mol-% of tertiary amine, based on tertiary amine used, and b) the second stirred tank is continuously supplied with a further amount of alkali metal hydroxide which is in the range from the remainder of the stoichiometric amount of alkali metal hydroxide remaining from the first tank up to an excess of 5 mol-%, and in this tank at a temperature of 60 to 100° C. a residence time is maintained such that the aqueous betaine solution leaving the tank contains less than 2 mol-% of tertiary amine, based on tertiary amine used, where, when three stirred tanks are used, the third is used for a following reaction at a temperature of 70 to 100° C. in order to obtain an aqueous betaine solution which, in comparison with the betaine solution from the second stirred tank, has a still lower content of tertiary starting amine.

2. The process as claimed in claim 1, wherein a) the first stirred tank is supplied simultaneously and continuously with the tertiary amine of said Formula 2 and the ω-halocarboxylic acid in an amount of 1 to 1.15 mol per mole of tertiary amine, the alkali metal hydroxide in an amount of only 0.85 to 0.95 mol per mole of ω-halocarboxylic acid and the water in an amount such that the betaine content of the finished aqueous betaine solution is 25 to 40% by weight, and in this tank at a temperature of 70 to 95° C. a residence time is maintained such that the product leaving this tank and entering the second stirred tank still contains 3 to 10 mol-% of tertiary amine, based on tertiary amine used, and b) the second stirred tank is continuously supplied with a further amount of alkali metal hydroxide which is in the range from the remainder of the stoichiometric amount of alkali metal hydroxide remaining from the first tank up to an excess of 3 mol-%, and in this tank at a temperature of 70 to 95° C. a residence time is maintained such that the aqueous betaine solution leaving the tank contains less than 2 mol-% of tertiary amine, based on tertiary amine used, where, when three stirred tanks are used, the third is used for a following reaction at a temperature of 80 to 100° C. in order to obtain an aqueous betaine solution which, in comparison with the betaine solution from the second stirred tank, has a still lower content of tertiary starting amine.

3. The process as claimed in claim 1, which comprises carrying out the reaction continuously in two stirred tanks arranged in a cascade and proceeding in such a way that a) the first stirred tank is supplied simultaneously and continuously with the tertiary amine of said Formula 2 and the ω-halocarboxylic acid in an amount of 1 to 1.15 mol per mole of tertiary amine, the alkali metal hydroxide in an amount of only 0.85 to 0.95 mol per mole of ω-halocarboxylic acid and the water in an amount such that the betaine content of the finished aqueous betaine solution is 25 to 40% by weight, and in this tank at a temperature of 70 to 95° C. a residence time is maintained such that the product leaving this tank and entering the second stirred tank still contains 3 to 10 mol-% of tertiary amine, based on tertiary amine used, and b) the second stirred tank is continuously supplied with a further amount of alkali metal hydroxide which is in the range from the residue of the stoichiometric amount of alkali metal hydroxide remaining from the first tank up to an excess of 3 mol-%, and in this tank at a temperature of 70 to 95° C. a residence time is maintained such that the aqueous betaine solution leaving the tank contains less than 2 mol-% of tertiary amine, based on tertiary amine used.

4. The process as claimed in claim 1, which comprises carrying out the reaction continuously in three stirred tanks arranged in a cascade and proceeding in such a way that
   a) the first stirred tank is supplied simultaneously and continuously with the tertiary amine of said Formula 2 and the ω-halocarboxylic acid in an amount of 1 to 1.15 mol per mole of tertiary amine, the alkali metal hydroxide in an amount of only 0.85 to 0.95 mol per mole of ω-halocarboxylic acid and the water in an amount such that the betaine content of the finished aqueous betaine solution is 25 to 40% by weight, and in this tank at a temperature of 70° to 95° C. a residence time is maintained such that the product leaving this tank and entering the second stirred tank still contains 3 to 10 mol-% of tertiary amine, based on tertiary amine used,
   b) the second stirred tank is continuously supplied with the remainder of the stoichiometric amount of alkali metal hydroxide remaining from the first tank, and in this tank at a temperature of 70° to 95° C. a residence time is maintained such that the product leaving this tank and entering the third tank contains less than 2 mol-% of tertiary amine, based on tertiary amine used, and
   c) the third stirred tank is continuously supplied with a further amount of alkali metal hydroxide up to a stoichiometric excess of 3 mol-%, and in this tank, at a temperature of 80° to 100° C. a residence time is maintained such that the aqueous betaine solution leaving the tank contains a still lower molar percentage of tertiary amine than the betaine solution entering the tank.

5. The process as claimed in claim 1, wherein a residence time is maintained in he second stirred tank such that the aqueous betaine solution leaving the tank contains less than 1 mol-% of tertiary amine, based on tertiary amine of said Formula 2 used.

6. The process as claimed in claim 2, wherein a residence time is maintained in the second stirred tank such that the aqueous betaine solution leaving the tank contains less than 1 mol-% of tertiary amine, based on tertiary amine used.

7. The process as claimed in claim 3, wherein a residence time is maintained in the second stirred tank such that the aqueous betaine solution leaving the tank contains less than 1 mol-% of tertiary amine, based on tertiary amine used.

8. The process as claimed in claim 4, wherein a residence time is maintained in the second stirred tank such that the aqueous betaine solution leaving the tank contains less than 1 mol-% of tertiary amine, based on tertiary amine used.

9. The process as claimed in claim 1, wherein the tertiary amine used is one of those of the formula 2, in which: $R^1$ is an alkyl radical having 8 to 18 carbon atoms or is a radical of the formula $R'CONH(CH_2)_z-$, in which R' has the meaning of $R^1$ and z is 2, 3 or 4, $R^2$ is an alkyl radical having 1 to 4 carbon atoms and $R^3$ is likewise an alkyl radical having 1 to 4 carbon atoms, the ω-halocarboxylic acid used is monochloroacetic acid and the alkali metal hydroxide used in potassium hydroxide or sodium hydroxide.

10. The process as claimed in claim 2, wherein the tertiary amine used is one of those of said formula 2, in which: $R^1$ is an alkyl radical having 8 to 18 carbon atoms or is a radical of the formula $R'CONH(CH_2)_z-$, in which R' has the meaning of $R^1$ and z is 2, 3 or 4, $R^2$ is an alkyl radical having 1 to 4 carbon atoms and $R^3$ is likewise an alkyl radical having 1 to 4 carbon atoms, the ω-halocarboxylic acid used is monochloroacetic acid and the alkali metal hydroxide used in potassium hydroxide or sodium hydroxide.

11. The process as claimed in claim 3, wherein the tertiary amine used is one of those of said formula 2, in which: $R^1$ is an alkyl radical having 8 to 18 carbon atoms or is a radical of the formula $R'CONH(CH_2)_z-$, in which R' has the meaning of $R^1$ and z is 2, 3 or 4, $R^2$ is an alkyl radical having 1 to 4 carbon atoms and $R^3$ is likewise an alkyl radical having 1 to 4 carbon atoms, the ω-halocarboxylic acid used is monochloroacetic acid and the alkali metal hydroxide used in potassium hydroxide or sodium hydroxide.

12. The process as claimed in claim 4, wherein the tertiary amine used is one of those of said formula 2, in which: $R^1$ is an alkyl radical having 8 to 18 carbon atoms or is a radical of the formula $R'CONH(CH_2)_z-$, in which R' has the meaning of $R^1$ and z is 2, 3 or 4, $R^2$ is an alkyl radical having 1 to 4 carbon atoms and $R^3$ is likewise an alkyl radical having 1 to 4 carbon atoms, the ω-halocarboxylic acid used is monochloroacetic acid and the alkali metal hydroxide used in potassium hydroxide or sodium hydroxide.

13. The process as claimed in claim 5, wherein the tertiary amine used is one of those of said formula 2, in which: $R^1$ is an alkyl radical having 8 to 18 carbon atoms or is a radical of the formula $R'CONH(CH_2)_z-$, in which R' has the meaning of $R^1$ and z is 2, 3 or 4, $R^2$ is an alkyl radical having 1 to 4 carbon atoms and $R^3$ is likewise an alkyl radical having 1 to 4 carbon atoms, the ω-halocarboxylic acid used is monochloroacetic acid and the alkali metal hydroxide used in potassium hydroxide or sodium hydroxide.

* * * * *